United States Patent
Lee et al.

(10) Patent No.: US 10,349,835 B2
(45) Date of Patent: Jul. 16, 2019

(54) OPTICAL SWITCHING UNIT, OPTICAL PROBE INCLUDING THE SAME, AND MEDICAL IMAGING APPARATUS INCLUDING OPTICAL PROBE

(71) Applicant: Samsung Electronics Co., Ltd., Suwon-si (KR)

(72) Inventors: Seung-wan Lee, Suwon-si (KR); Woon-bae Kim, Seoul (KR); Eun-sung Lee, Hwaseong-si (KR); Jong-hyeon Chang, Suwon-si (KR); Min-seog Choi, Seoul (KR); Hyun Choi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 621 days.

(21) Appl. No.: 14/475,072

(22) Filed: Sep. 2, 2014

(65) Prior Publication Data

US 2015/0126874 A1 May 7, 2015

(30) Foreign Application Priority Data

Nov. 1, 2013 (KR) ........................ 10-2013-0132528

(51) Int. Cl.
  *A61B 1/00* (2006.01)
  *A61B 1/07* (2006.01)
  *A61B 5/00* (2006.01)

(52) U.S. Cl.
  CPC ........ *A61B 5/0084* (2013.01); *A61B 1/00096* (2013.01); *A61B 1/07* (2013.01); *A61B 5/0066* (2013.01); *A61B 5/0095* (2013.01)

(58) Field of Classification Search
  None
  See application file for complete search history.

(56) References Cited

U.S. PATENT DOCUMENTS

| 4,898,470 A | 2/1990 | Cleaveland |
| 4,961,069 A * | 10/1990 | Tsaprazis ............ G01F 23/2925 250/577 |
| 6,134,003 A | 10/2000 | Tearney et al. |
| 2002/0037130 A1 * | 3/2002 | McBride .............. G02B 6/3538 385/16 |

(Continued)

OTHER PUBLICATIONS

Ford et al., "Optical coherence tomography for endoscopes, using imaging fibre bundles and a conical mirror", 22$^{nd}$ International Conference on Optical Fiber Sensors, Proceedings of SPIE vol. 8421, 2012, 4 pages.

*Primary Examiner* — Carolyn A Pehlke
(74) *Attorney, Agent, or Firm* — Sughrue Mion, PLLC (57) ABSTRACT

Provided are an optical switch, an optical probe including the optical switch, and a medical imaging apparatus including the optical probe. The optical probe includes a probe body that is configured to be insertable into a body cavity, and an optical switch that is disposed in the probe body and includes a first region formed of a material having a first refractive index, and a second region that forms an interface with the first region and is configured to have a fluid is introduced into the second region, wherein the optical switch is configured to change a path of propagation of incident light according to a second refractive index of the second region.

20 Claims, 10 Drawing Sheets (56) References Cited

U.S. PATENT DOCUMENTS

2007/0066871 A1\* 3/2007 Yang ................. A61B 1/00096
600/173
2008/0221388 A1 9/2008 Seibel et al.
2012/0099112 A1\* 4/2012 Alphonse ........... G01B 9/02091
356/479

\* cited by examiner

OPTICAL SWITCHING UNIT, OPTICAL PROBE INCLUDING THE SAME, AND MEDICAL IMAGING APPARATUS INCLUDING OPTICAL PROBE

RELATED APPLICATION

This application claims priority from Korean Patent Application No. 10-2013-0132528, filed on Nov. 1, 2013, in the Korean Intellectual Property Office, the disclosure of which is incorporated herein by reference in its entirety.

BACKGROUND

1. Technical Field

Systems, methods, and apparatuses consistent with exemplary embodiments relate to an optical switch, an optical probe including the same, and a medical imaging apparatus including the optical probe.

2. Description of the Related Art

In medical imaging fields, imaging techniques such as magnetic resonance imaging (MRI), computed tomography (CT) imaging, and ultrasound imaging may create cross-sectional images of the inside of a body by penetrating a skin. However, because these imaging techniques may have resolutions that are too low for a person of ordinary skill in the art to use in attempting to detect a cancer at an early stage. Further, in addition to the imaging techniques noted above, recent technological development has led to the development of imaging techniques such as optical coherence tomography (OCT), optical coherence microscopy (OCM), and photoacoustic tomography (PAT) that uses light that penetrates into the skin to a small depth, e.g., 1 to 2 mm (OCT) or 30 to 50 mm (PAT). These techniques may achieve, for example, resolutions that are about 10 times higher than ultrasound imaging, thereby these imaging techniques may help allow earlier detection of, for example, a cancer.

SUMMARY

According to an aspect of an exemplary embodiment, there is provided an optical probe including a probe body that is configured to be insertable into a body cavity, and an optical switch that is disposed in the probe body and includes a first region formed of a material having a first refractive index, and a second region that forms an interface with the first region and is configured to have a fluid is introduced into the second region, wherein the optical switch is configured to change a path of propagation of incident light according to a second refractive index of the second region.

The interface may include a shape tapered in a longitudinal direction of the probe body.

The interface may be symmetric about a central axis of the probe body.

The optical probe may further include an optical fiber for delivering light to the optical switch, wherein a width of the interface decreases toward the optical fiber.

An angle between the interface and the central axis of the probe body may be less than or equal to 90°−θi where θi is a critical angle for total reflection at the interface.

Light may propagate along a longitudinal direction of the probe body in response to the second refractive index of the fluid being introduced into the second region of the optical switch being the same as the first refractive index, and At least part of the light may propagate in a lateral direction of the probe body in response to the fluid introduced into the second region having the second refractive index that is different from the first refractive index.

The second region may be formed in-between a transparent plate located opposite the interface.

An opening through which the fluid flows to the second region maybe formed between the interface and the transparent plate.

The light may be incident on a surface of the first region that is opposite the interface.

The light may be incident perpendicularly on the surface of the first region that is opposite the interface.

A first fluid having the first refractive index and a second fluid having the second refractive index that is less than the first refractive index may be selectively introduced into the second region.

The first fluid may be a transparent liquid, and the second fluid is a transparent gas.

The second fluid may be the same as fluid present in the probe body.

The light may be incident perpendicularly on a surface of the second region that is opposite to the interface.

A third fluid having the first refractive index and a fourth fluid having the second refractive index greater than the first refractive index may be selectively introduced into the second region.

The first region may be formed of a transparent solid material including at least one of plastic and glass.

According to an aspect of another exemplary embodiment, there is provided an optical switch including a first region formed of a material having a first refractive index, and a second region that forms an interface with the first region and into which a fluid is configured to be introduced, wherein a path of propagation of incident light is changed according to a refractive index of the second region.

The interface may include a shape tapered in a direction across the first and second regions.

The interface may be symmetric about a central axis across the first and second regions.

An angle between the interface and the central axis may be less than or equal to 90°−θi where θi is a critical angle for total reflection at the interface.

The path of propagation of the incident light may remain unchanged in response to the fluid having the first refractive index being introduced into the second region.

The path of propagation of the incident light may be changed in response to the fluid having a refractive index different from the first refractive index being introduced into the second region.

The second region may be formed by a transparent plate opposite to the interface.

A first fluid having the first refractive index and a second fluid having a second refractive index less than the first refractive index may be selectively introduced into the second region.

The first fluid may be a transparent liquid, and the second fluid is a transparent gas.

According to an aspect of another exemplary embodiment, there is provided an optical switch including a first region, and a conical mirror that is adjacent to a surface of the first region, wherein a path of propagation of light is changed when the light is incident on the conical mirror.

According to an aspect of another exemplary embodiment, there is provided a medical imaging apparatus including a light source for generating light, an optical probe including a probe body that is configured to be insertable into a body cavity, and an optical switch that is disposed in the probe body and includes a first region formed of a material having a first refractive index, and a second region that forms an interface with the first region and is configured to have a fluid is introduced into the second region, wherein the optical switch is configured to change a path of propagation of incident light according to a second refractive index of the second region, and wherein the optical probe is configured to irradiates light generated by the light source onto an object.

The optical probe may illuminate the object, and the apparatus may be an endoscope.

The apparatus may further include a beam splitter configured to split the light generated by the light source into a measurement beam and a reference beam, send the measurement beam to the optical probe, and receive a responding beam corresponding to the measurement beam from the optical probe, and wherein the apparatus uses optical coherence tomography (OCT).

According to an aspect of another exemplary embodiment, there is provided an optical probe configured to be used in an endoscope, the optical probe including an optical switch configured to be connected at an end of the optical probe, wherein the optical switch comprises, a first region with a first refractive index, a second region with a second refractive index and an interface between the first region and the second region configured to guide propagation of incident light through at least one of the first region and the second region based on the first refractive index, the second refractive index, and a shape and a position of the interface.

The first region may include a first exterior housing with a first internal cavity configured to hold a first fluid, wherein the first fluid is moved through a first opening in the first exterior housing that is connected to a first fluid flow path connected to a probe body.

The first exterior housing may be a malleable material that expands to a predetermined shape when filled with the first fluid and deflates when the first fluid is removed.

The second region may include a second exterior housing with a second internal cavity configured to hold a second fluid, wherein the second fluid is moved through a second opening in the second exterior housing that is connected to a second fluid flow path connected to the probe body.

The second exterior housing may be a malleable material that expands to a predetermined shape when filled with the second fluid and deflates when the second fluid is removed.

The shape and the position of the interface may change based on the amount of fluid in the first region and the second region.

BRIEF DESCRIPTION OF THE DRAWINGS

These and/or other aspects will become more apparent and more readily appreciated from the following description of exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. Dimensions of components in the drawings may be exaggerated for clarity and convenience of explanation. Expressions such as "at least one of," when preceding a list of elements, modify the entire list of elements and do not modify the individual elements of the list.

Figure 1:
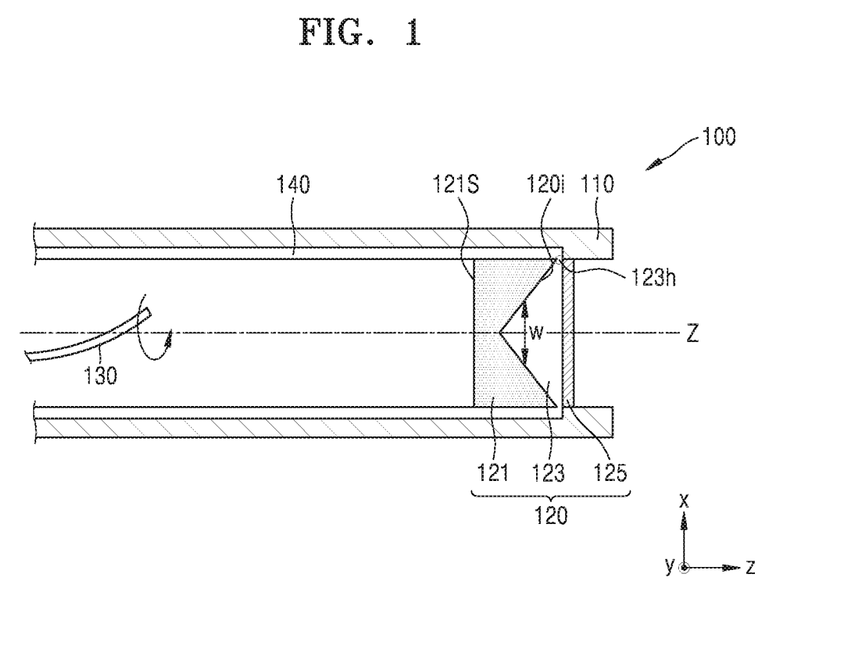
FIG. 1 is a schematic diagram of an optical probe according to an exemplary embodiment.

FIG. 1 is a schematic diagram of an optical probe 100 according to an exemplary embodiment. Referring to FIG. 1, the optical probe 100 according to an exemplary embodiment includes a probe body 110 that can be inserted into a body cavity and an optical switch 120 that changes the path of propagation of light received through the interior of the probe body 110 according to a refractive index of a fluid.

At least a part of the probe body 110 may be inserted into a body cavity. The probe body 110 has an empty space in which the optical switch 120 is disposed. Due to its structure, the probe body 110 may irradiate an object inside a body cavity with light or receive a signal (e.g., light, ultrasound waves, etc.) reflected from the object. The probe body 110 may be made of a transparent material so that light is emitted towards a side thereof as well. The whole area of the probe body 110 is not necessarily formed of a transparent material. Only regions of the probe body 110 that are adjacent to the optical switch 120 may be made of a transparent material. Although the optical switch 120 is disposed within the probe body 110, the exemplary embodiment is not limited thereto. For example, the optical switch 120 may be disposed at an upper end of the probe body 110 or between a plurality of probe bodies 110. According to another exemplary embodiment an optical switch may be attached at a terminating end of a probe body through which an optical fiber carries light to the optical switch such that the optical switch protrudes out from the probe body.

The optical probe 100 may further include an optical fiber 130 that transmits light to the optical switch 120. Light transmitted by the optical switch 120 may be light from a laser. The optical fiber 130 may be fixed in a predetermined region so as to emit light along a predetermined path, or the shape of the optical fiber 130 may be modified so as to emit light along different paths. Optical scanning from the optical fiber 130 will be described in detail below.

The optical switch 120 may include a first region 121 having a first refractive index and a second region 123 into which a fluid may flow. The first region 121 may be formed of a transparent solid material with the first refractive index. For example, the first region 121 may be formed of a material containing at least one of plastic and glass. A surface 121S of the first region 121 opposite to the optical fiber 130 may be perpendicular to a longitudinal (z-axis) direction of the optical probe 100. Furthermore, an interface 120$i$ between the first and second regions 121 and 123 may be tapered in a longitudinal (z-axis) direction of the probe body 110. For example, a width w of the interface 120$i$ may decrease toward the optical fiber 130. The interface 120$i$ may have a horn shape directed toward the optical fiber 130. The interface 120$i$ in a plane (xy plane) perpendicular to the longitudinal (z-axis) direction of the probe body 110 may have a circular, elliptical, or polygonal cross-section, but is not limited thereto. The interface 120$i$ may also be symmetric about a central axis Z of the probe body 110.

The second region 123 may be a space formed by the interface 120$i$ and a transparent plate 125 opposite to the interface 120$i$. The optical probe 100 may further include a connector for connecting the interface 120$i$ with the transparent plate 125. For example, the interface 120$i$, the transparent plate 125, and a region of the probe body 110 for connecting the interface 120$i$ with the transparent plate 125 may cooperate to form the second region 123. The second region 123 may include at least one opening 123$h$ through which a fluid flows in and out. The opening 123$h$ may be connected to a fluid reservoir through a fluid flow path 140, which may also be called a channel or chamber, such that a plurality of different fluids, each having different refractive indices, may be selectively introduced into the second region 123. The plurality of fluids may not be mixed with one another. For example, one of the fluids may be a polar liquid, and another one may be a gas or a non-polar liquid. The fluids may be light-transmissive. For example, fluids having refractive indices that are the same as and different from the first refractive index may be selectively introduced into the second region 123.

The optical probe 100 may further include a lens array including at least one lens, which is disposed between the optical fiber 130 and the optical switch 120 so as to allow light emitted from the optical fiber 120 to be normally incident on the optical switch 120. The lens array may include a collimator lens or graded index (GRIN) lens.

Figure 2A:
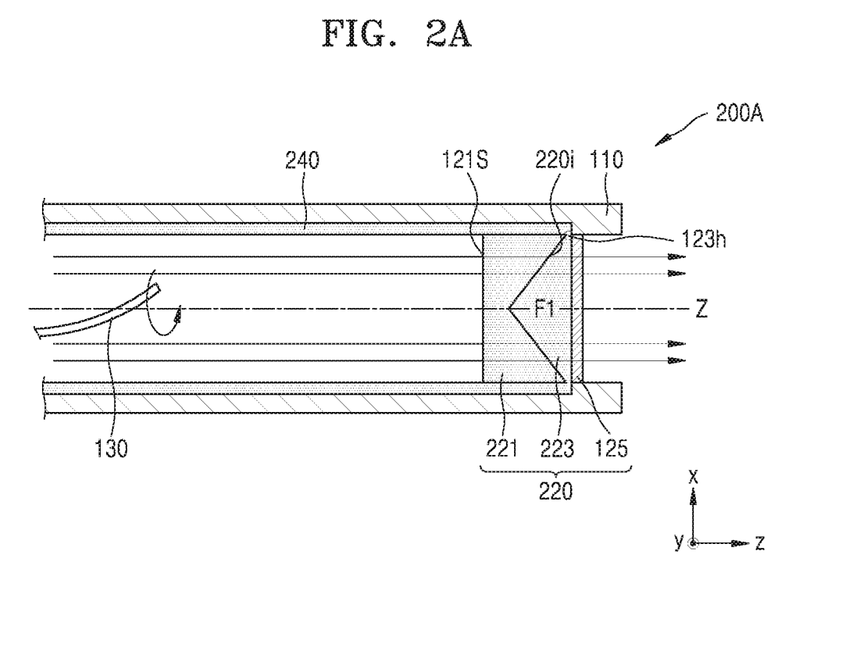
FIGS. 2A and 2B illustrate paths of propagation of light according to a refractive index of a fluid introduced into an optical switch.
Figure 2B:
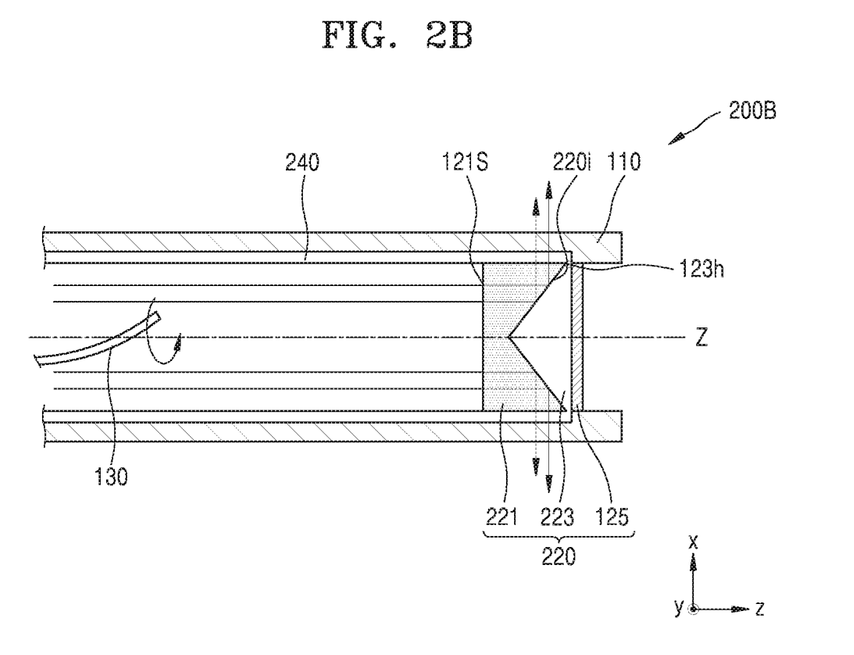

FIGS. 2A and 2B illustrate paths of propagation of light according to a refractive index of a fluid introduced into an optical switch 220, similar to that shown in FIG. 1.

A first fluid F1 having a first refractive index may be introduced into a second region 223 through a chamber 240. The first fluid F1 may be a transparent liquid. Because a first and second regions 221 and 223 are filled with a material having the first refractive index, as shown in FIG. 2A, light incident on the first region 221 sequentially passes through the first and second regions 221 and 223 and propagates along a longitudinal (z-axis) direction of an optical probe 200A and/or 200B. In other words, a path of propagation of light that enters the optical switch 220 remains unchanged. A second fluid F2 having a second refractive index less than the first refractive index may also be introduced into the second region 223. The second fluid F2 may be the same as a fluid present in the optical probe 200A and/or 200B, and may be a transparent gas. For example, the second fluid F2 may be air. In this case, because the first and second regions 221 and 223 are filled with materials having different refractive indices, at least part of light incident on the first region 221 may be reflected off the interface 220$i$ between the first and second regions 221 and 223. In particular, when light incident on the interface 220$i$ satisfies the condition for total reflection according to Snell's law, a path of propagation of light may be changed so that the light is totally reflected off the interface 220$i$ and emitted in a lateral direction of the optical probe 100. For example, when the interface 220$i$ in a direction parallel to the longitudinal (z-axis) direction of the optical probe 100 is a straight line, an angle between the interface 220$i$ and the central axis Z of the probe body 110 may be less than or equal to 90°−θi where θi is a critical angle for total reflection at the interface 220$i$.

In this manner, the optical switch 220 may transmit light in the longitudinal (z-axis) direction or in the lateral direction of the optical probe 200A and/or 200B according to a refractive index of a fluid that is introduced into the second region 223. Thus, the optical probe 100 according to the present exemplary embodiment may use a forward-view mode or a side-view mode.

Figure 3A:
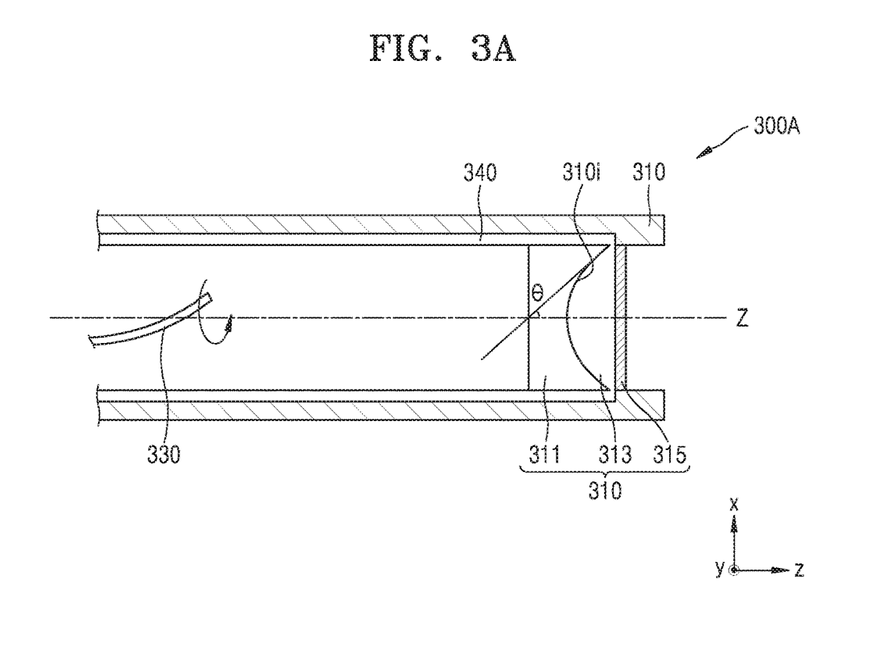
FIGS. 3A through 3D illustrate modified examples of an optical switch according to one or more exemplary embodiments.

FIGS. 3A through 3D illustrate modified examples of an optical switch according to an exemplary embodiment. Referring to FIG. 3A, an interface 310$i$ in a direction parallel to a longitudinal (z-axis) direction of a probe body 310 may be a curve. For example, an angle θ between a tangent line to the interface 310$i$ and a central axis Z of the probe body 310 may increase as the interface 310$i$ becomes closer to the central axis Z thereof. When a first fluid F1 having a refractive index equal to a first refractive index flows into a second region 313 from or through a channel 340, an optical switch 310 emits light in the longitudinal (z-axis) direction of the probe body 310. Light may be transmitted through a first region 311 then refract according to the materials of the first and second regions 311 and 313 as the light passes through the interface 310$i$. Then the portion of the light that propagates through the second region 313 will then travel through a transparent plate 315 as it leaves, or enters, the optical probe 300A. On the other hand, when a second fluid F2 having a refractive index less than the first refractive index flows into the second region 313, the optical switch 310 may emit light in the longitudinal (z-axis) or lateral direction of the probe body 310 according to the position of incident light.

For example, light is emitted in the lateral direction of the probe body 310 by total reflection at a region where the angle θ between a tangent line to the interface 310$i$ and the central axis Z of the probe body 310 is less than or equal to 90°−θi where θi is a critical angle for total reflection at the interface 310$i$. On the other hand, at a region where the angle θ between a tangent line to the interface 310$i$ and the central axis Z of the probe body 310 exceeds 90°−θi, light is emitted in the longitudinal (z-axis) direction of the probe body 310.

Figure 3B:
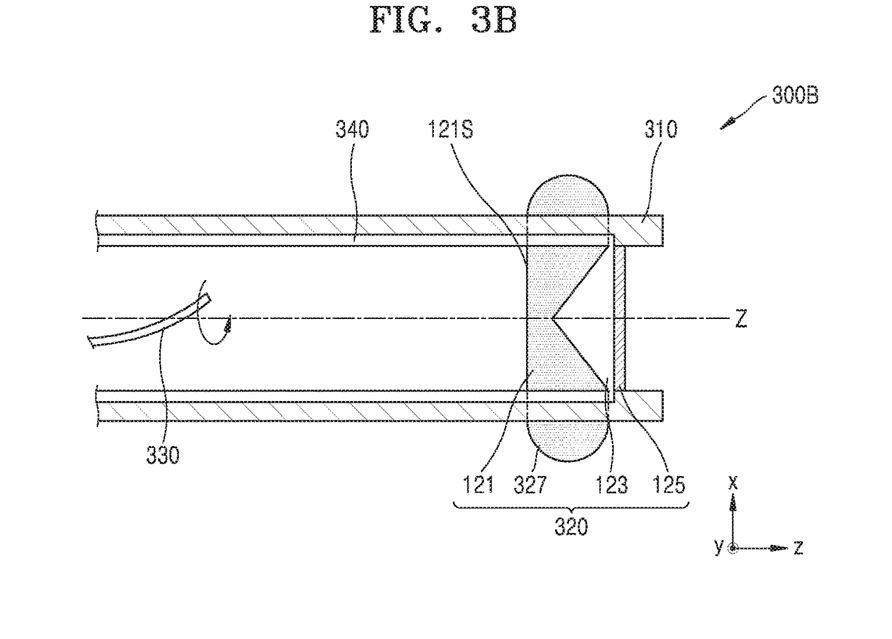
Figure 3C:
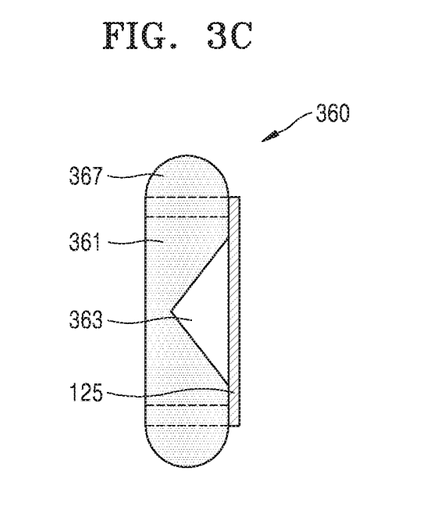

Referring to FIG. 3B, an optical switch 320 may further include a light focusing element 327 that is disposed at sides of the probe body 310 and focuses externally emitted light. The light focusing element 327 may be a convex lens or tubular lens. Alternatively, as shown in FIG. 3C, an optical switch 360 may have a first region 361 and a light focusing element 367 integrally formed with each other. An opening through which a fluid flows in or out is formed in a second region 363.

Figure 3D:
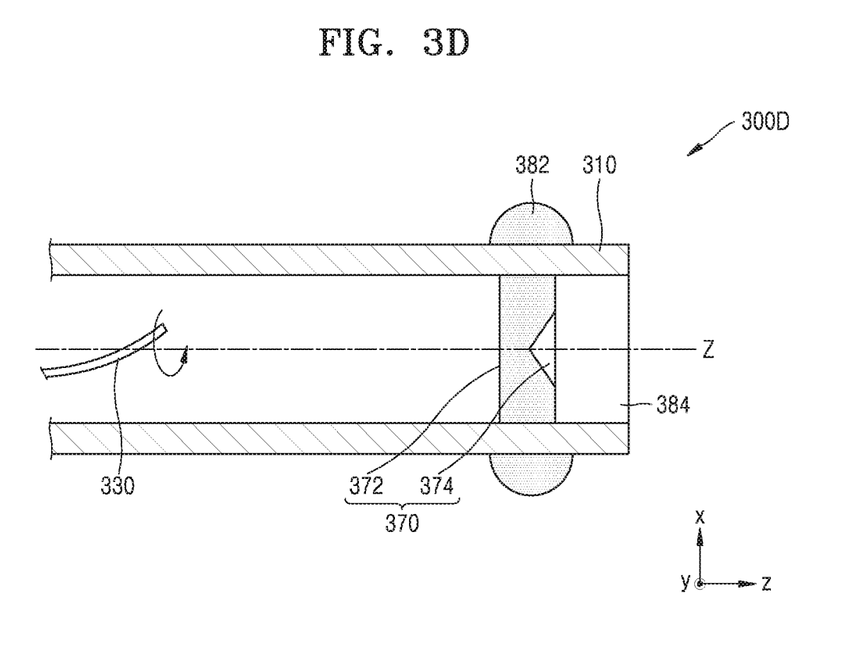

In another exemplary embodiment, as shown in FIG. 3D, an optical fiber 330 may be formed of a material that makes light parallel. An optical switch 370 may include a small conical mirror 374 at its center. A surface of the conical mirror 374 may be formed of a metal having high reflectivity. For example, the optical switch 370 may include a first region 372 and the conical mirror 374 as a second region. The mirror 374 may be in contact with only a portion of the first region 372. In detail, only sides of the conical mirror 374 may contact the first region 372. An optical probe 300D may further include a first light focusing element 382 disposed at sides thereof and a second light focusing element 384 disposed therein. Thus, light passing through the first region 372 to the conical mirror 374 is reflected so that it propagates in a lateral direction of the probe body 310 while light passing only through the first region is emitted in a longitudinal (z-axis) direction of the probe body 310.

Figure 4:
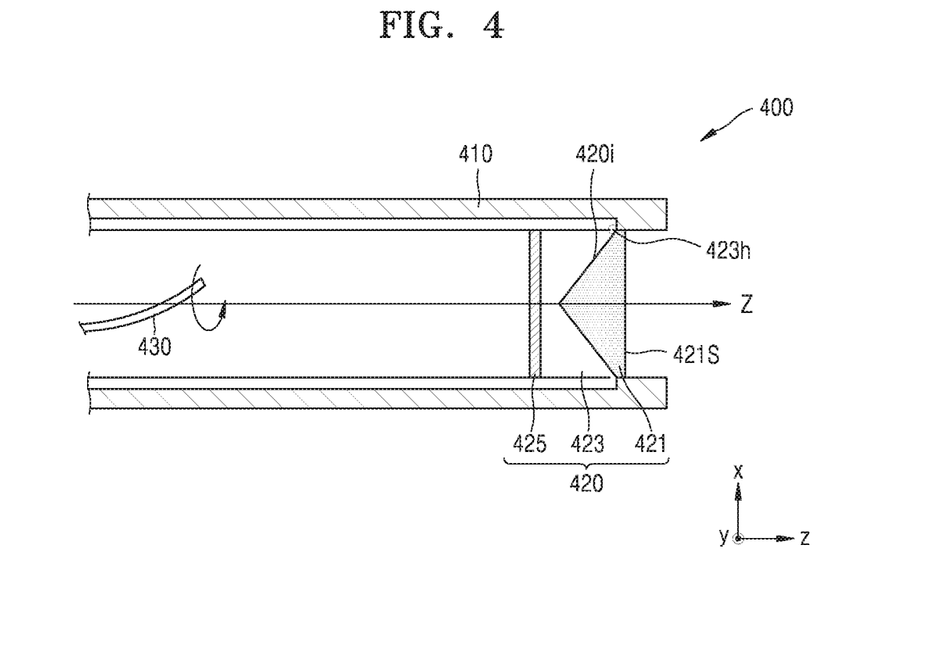
FIG. 4 is a schematic diagram of an optical probe according to another exemplary embodiment.

FIG. 4 is a schematic diagram of an optical probe 400 according to another exemplary embodiment. The optical probe 400 is different from the optical probe 100 of FIG. 1 in that an optical switch 420 includes a first region 421 and a second region 423 disposed at positions corresponding to the second region 123 and the first region 121 shown in FIG. 1, respectively. For example, the second region 423 into which a fluid may be introduced and the first region 421 having a first refractive index are sequentially arranged along a path of propagation of light. Due to this arrangement, light delivered by an optical fiber 430 enters the second region 423, and it may propagate in a longitudinal (z-axis) or lateral direction of the optical probe 400 according to a difference in refractive index between the first and second regions 421 and 423.

In detail, the first region 421 may be formed of a transparent solid material having the first refractive index. For example, the first region 421 may be formed of a material containing at least one of plastic and glass. An interface 420i between the first and second regions 421 and 423 may be tapered in a longitudinal (z-axis) direction of a probe body 410. For example, a width of the interface 420i may decrease toward the optical fiber 430. The interface 420i may have a horn shape directed toward the optical fiber 430. The interface 420i in a direction perpendicular to the longitudinal (z-axis) direction of the probe body 410 may have a circular, elliptical, or polygonal cross-section, but is not limited thereto. The interface 420i may also be symmetric about a central axis Z of the probe body 410.

The second region 423 may be a space formed by the interface 420i and a transparent plate 425 opposite to the interface 420i. The transparent plate 425 is disposed between the interface 421i and the optical fiber 430 and transmits light delivered by the optical fiber 430 to the second region 423. The transparent plate 425 may be disposed so that light is normally incident thereon. A surface 421S of the first region 421 opposite to the interface 420i may be parallel to the transparent plate 425.

The optical probe 400 may further include a connector for connecting the interface 420i with the transparent plate 425. For example, the interface 420i, the transparent plate 425, and a region of the probe body 110 for connecting the interface 420i with the transparent plate 425 may cooperate to form the second region 423. The second region 423 may also include at least one opening 423h through which a fluid flows in and out. The opening 423h may be connected to a fluid reservoir through a fluid flow path so that a plurality of fluids having different refractive indices may be selectively introduced into the second region 423. The plurality of fluids may not be mixed with one another. For example, one of the fluids may be a polar liquid, and another one may be a gas or a non-polar liquid. The fluids may be light-transmissive. For example, fluids having refractive indices that are the same as and different from the first refractive index may be selectively introduced into the second region 423.

Figure 5A:
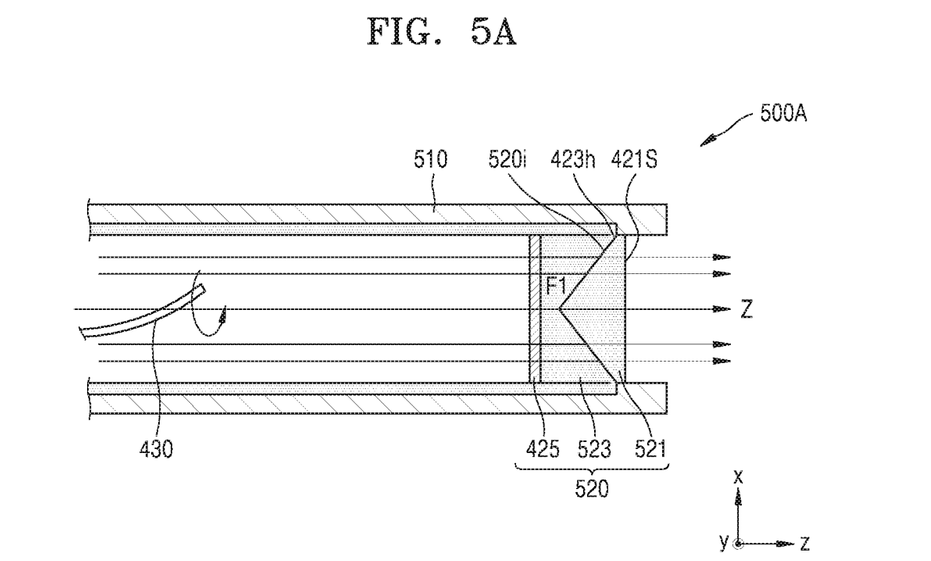
FIGS. 5A through 5C illustrate paths of propagation of light according to a refractive index of a fluid introduced into an optical switch, similar to that shown in FIG. 4, according to one or more exemplary embodiments.
Figure 5B:
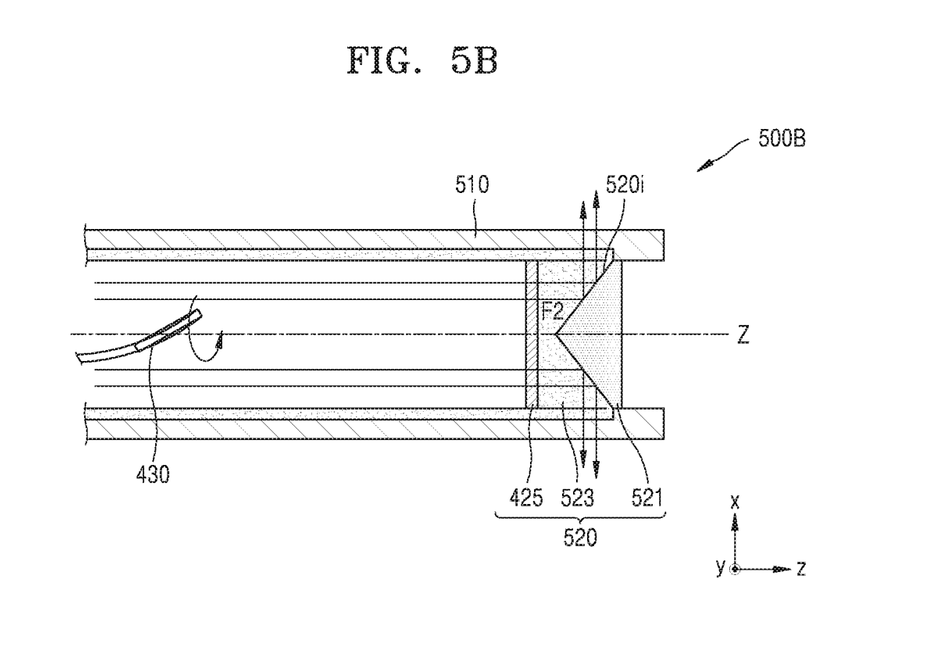
Figure 5C:
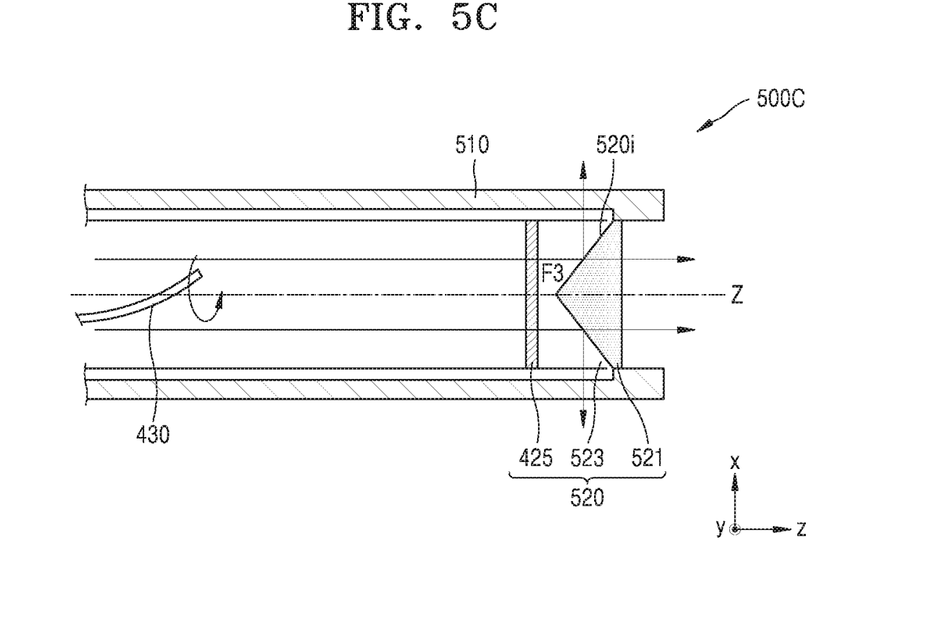

FIGS. 5A through 5C illustrate paths of propagation of light according to a refractive index of a fluid introduced into an optical switch 520, similar to the optical switch 420 shown in FIG. 4. A first fluid F1 having a first refractive index may be introduced into a second region 523. The first fluid F1 may be a transparent liquid. Because the first and second regions 521 and 523 are filled with a material having the first refractive index, as shown in FIG. 5A, light incident on the second region 523 sequentially passes through the second and first regions 523 and 521 and propagates along a longitudinal (z-axis) direction of the probe body 510.

A second fluid F2 having a second refractive index less than the first refractive index may also be introduced into the second region 523. The second fluid F2 may be a transparent gas, and may be the same as a fluid present in the optical probe 500C. For example, the second fluid F2 may be air. In this case, as shown in FIG. 5B, part of light incident on the second region 523 may be transmitted at the interface 520i so that it propagates in the longitudinal (x-axis) direction of the optical probe 500B and is emitted in a forward direction of the probe body 510. Another part of light may be reflected off the interface 520i and emitted in a side direction of the probe body 510.

A third fluid F3 having a third refractive index greater than the first refractive index may also be introduced into the second region 523. The third fluid F3 may be a transparent liquid. In this case, because the first and second regions 521 and 523 are filled with materials having different refractive indices, light incident on the second region 523 may be reflected off the interface 520i between the first and second regions 521 and 523. In particular, when light incident on the interface 520i satisfies the condition for total reflection according to Snell's law, as shown in FIG. 5B, the light is totally reflected off the interface 520i and emitted in a lateral direction of the probe body 510. For example, if an angle between the interface 520i and the central axis Z of the probe body 510 may be less than or equal to 90°−θi where θi is a critical angle for total reflection at the interface 520i, light may be totally reflected off the interface 520i and emitted in the lateral direction of the probe body 510.

In this way, the optical switch 520 may change a path of propagation of light according to a refractive index of a fluid that is introduced into the second region 523. Thus, the optical probe 500A, 500B, and/or 500C according to the present exemplary embodiment may selectively or simultaneously use a forward-view mode and a side-view mode. The above-described optical switches 120, 310, 320, 330, 420, and 520 may be fabricated as separate devices and be mounted in the optical probes 100, 300a, 300b, 300c, 400, 500A, 500B, and 500C, respectively.

An optical probe according to an exemplary embodiment may further include an optical scan module (or optical scanner) for scanning light in a one- or two-dimensional manner. The optical scanner may change a position at which light is irradiated while the position of the optical probe itself remains unchanged.

According to another exemplary embodiment an optical probe, configured to be used in an endoscope, may include an optical switch configured to be connected at an end of the optical probe. The optical switch may include a first region with a first refractive index, a second region with a second refractive index; and an interface between the first region and the second region configured to guide propagation of incident light through at least one of the first region and the second region based on the first refractive index, the second refractive index, and a shape and a position of the interface.

Further, the first region may include a first exterior housing with a first internal cavity configured to hold a first fluid, wherein the first fluid is moved through a first opening in the first exterior housing that is connected to a first fluid flow path connected to a probe body. Similarly, the second region may include a second exterior housing with a second internal cavity configured to hold a second fluid, wherein the second fluid is moved through a second opening in the second exterior housing that is connected to a second fluid flow path connected to the probe body.

Additionally, the first exterior housing may be constructed from a malleable material that expands to a predetermined shape when filled with the first fluid and deflates when the first fluid is removed. The second exterior housing may also be constructed from a malleable material that expands to a predetermined shape when filled with the second fluid and deflates when the second fluid is removed. Further, the shape and the position of the interface may be adjusted by changing the shape and position based on the amount of fluid in the first region and the second region.

This exemplary embodiment may allow the optical probe to shrink and provide additional flexibility at the end where the optical switch is located allowing the probe to more easily enter and maneuver a body cavity. Then, when fluid is provided into the first and second regions, the optical probe and optical switch may expend to the predetermined size and shape. Further, the regions may be formed such that different amounts of fluid in each of the regions may provide different shapes that provide different optical properties for the light being transceived by the probe device.

Figure 6:
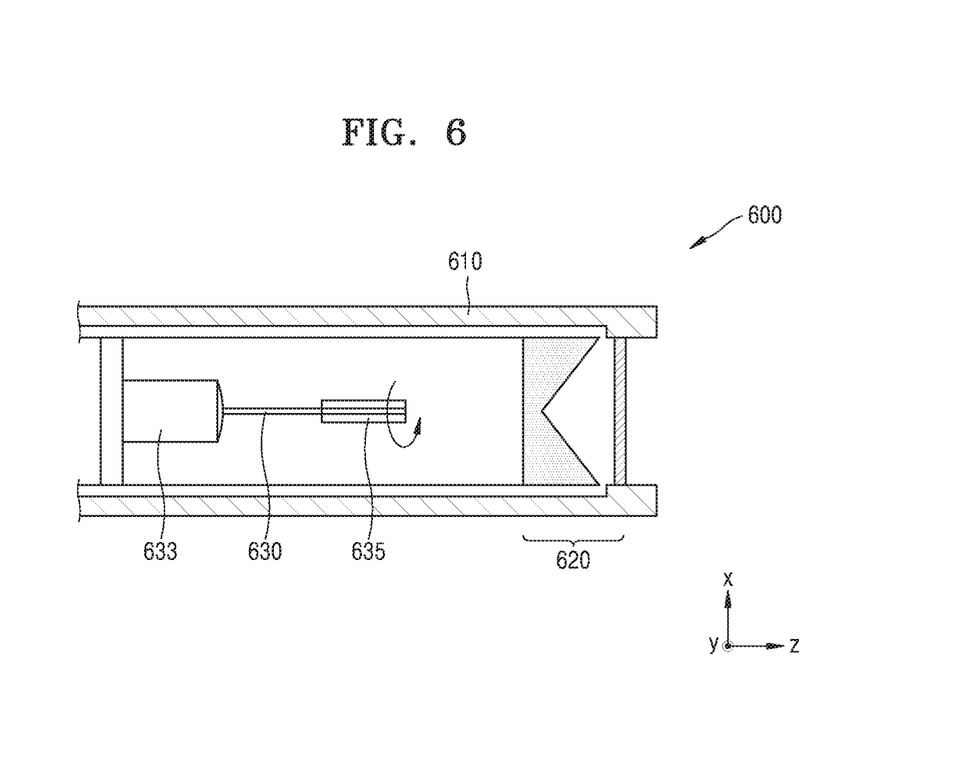
FIG. 6 illustrates an optical probe including an optical scanner according to an exemplary embodiment.

FIG. 6 illustrates an optical probe 600 including an optical scanner according to an exemplary embodiment. Referring to FIG. 6, the optical scanner for delivering light to an optical switch 620 is disposed within a probe body 610. The optical scanner includes an optical fiber 630, an actuator 633 for driving the optical fiber 630, and an asymmetric structure 635 attached to one side of the optical fiber 630.

The optical scanner is configured to scan light onto a certain area by inducing deformation of the optical fiber 630. To achieve this, the actuator 633 is driven with respect to two axes so that one end of the optical fiber 130 is deformed in two directions, e.g., x- and y-directions. For example, the actuator 633 may be a piezoelectric actuator using a piezoelectric material that changes its shape in response to an electrical signal.

The asymmetric structure 635 may be used to separate resonant frequencies in two axis directions when the optical fiber 630 is driven. When performing scanning by driving the optical fiber 630, the actuator 633 may drive the optical fiber 630 at a resonant frequency of a fiber-actuator system or a frequency range adjacent to the resonant frequency in order to achieve the maximum efficiency. Hereinafter, a 'fiber-actuator system' includes an actuator and all structures that are driven by the actuator, such as an optical fiber and an asymmetric structure coupled thereto. Because a resonant frequency of the fiber-actuator system is proportional to a bending moment of inertia, resonant frequencies in two-axis directions may be made different by varying bending moments of inertia in the two-axis directions. According to the present exemplary embodiment, in consideration of this, the asymmetric structure 635 designed to vary bending moments of inertia about two axes is mounted to the optical fiber 630 so that resonant frequencies in two-axis directions are different from each other. As shown in FIG. 6, the asymmetric structure 635 may include a hole or a groove into which the optical fiber 630 will be inserted to facilitate mounting, and may be formed of a material or have a shape that can adjust the resonant frequencies in the two-axis directions to certain frequencies. Although one asymmetric structure 635 is attached to the optical fiber 630, an exemplary embodiment is not limited thereto, and a plurality of asymmetric structures 635 may be mounted thereto.

Figure 7:
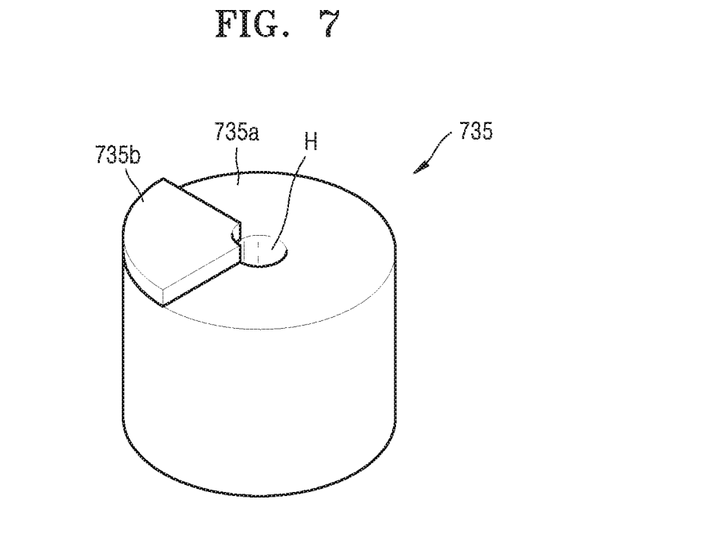
FIG. 7 illustrates an exemplary structure of an asymmetrical structure that can be used in an optical scanner, similar to that shown in FIG. 6, according to an exemplary embodiment.

FIG. 7 illustrates an exemplary structure of an asymmetrical structure 735 that may be used in the optical scanner 630 shown in FIG. 6.

The asymmetric structure 735 includes a cylinder 735a with a top surface partially etched to form a through-hole H penetrating a central part thereof. Furthermore, the asymmetric structure 735 further includes a pillar 735b having a truncated fan shape projecting upward from the cylinder 735a having the through-hole H formed therein. An angle or thickness of the pillar 735b may be determined in consideration of certain resonant frequencies in two-axis directions. The asymmetric structure 735 is designed to have a symmetrical cross-sectional shape and a non-uniform thickness in order to vary bending moments of inertia about two axes. Alternatively, to achieve this, the asymmetric structure 735 may have an asymmetric cross-sectional shape and a uniform thickness.

Figure 8:
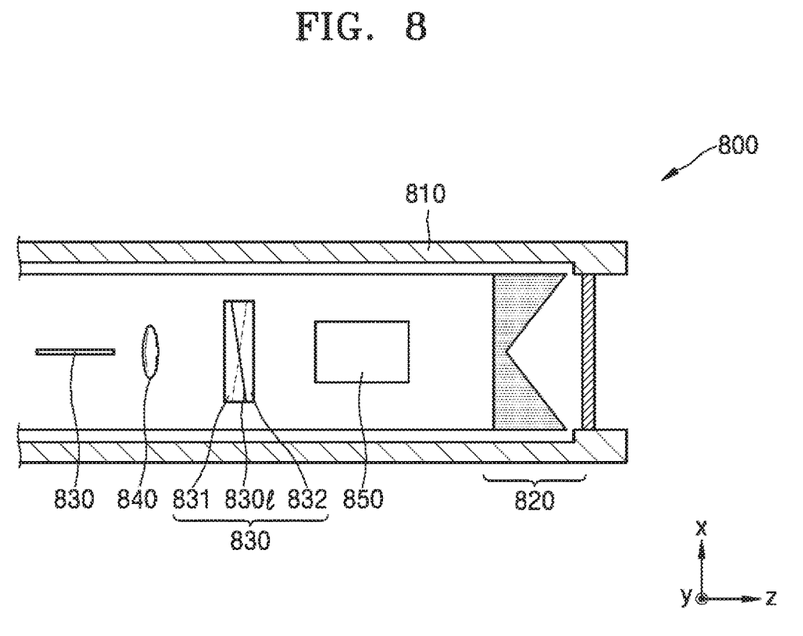
FIG. 8 illustrates an optical probe including an optical scanner according to another exemplary embodiment.
Figure 9:
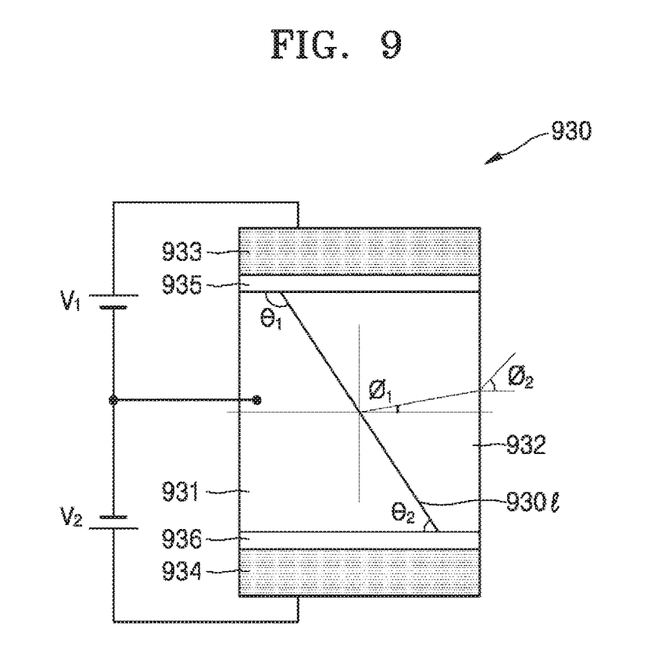
FIG. 9 is a detailed diagram of an optical scanner, similar to that shown in FIG. 8, according to an exemplary embodiment.

FIG. 8 illustrates an optical probe 800 including an optical scanner 830 according to another exemplary embodiment, and FIG. 9 is a detailed diagram of the optical scanner 930. The optical probe 800 according to the present exemplary embodiment differs from the optical probe 100 of FIG. 1 in that it may further include the optical scanner 830 disposed in a probe body 810 between an optical fiber 130 and an optical switch 820. The optical probe 800 may further include a first lens array 840 and a second lens array 850. The first lens array 840 is disposed between the optical fiber 130 and the optical scanner 830 and scatters light from the optical fiber 130 so that it is incident perpendicularly on the optical scanner 830. The second lens array 850 is disposed between the optical scanner 830 and the optical switch 820 and converges light emitted from the optical scanner 830 so that it is incident perpendicularly on the optical switch 820. The first lens array 840 may include a collimator lens while the second lens array 850 may include a GRIN lens.

Referring to FIGS. 8 and 9, the optical scanner 830 includes first and second fluids 831 and 832 having different refractive indices but not mixed together. The optical scanner 830 may scan light delivered through the optical fiber 130 in response to a change in an interface 830*l* between the first and second fluids 831 and 832.

In detail, the optical scanner 830 may include the first and second fluids 831 and 832 having different refractive indices. At least one of the first and second fluids 831 and 832 flows by using electrowetting so that a tilt angle $\Phi 1$ of the interface 830*l* between the first and second fluids 831 and 832 is changed. Light incident on the optical scanner 830 is then refracted at a different angle according to the tile angle $\Phi 1$ of the interface 830*l*. The angle of refraction at the interface 830*l* may be determined according to Snell's law. The refracted light is refracted again at an interface 832I between the second fluid 832 and the outside before leaving the optical scanner 830 at an exit angle $\Phi 2$. The exit angle $\Phi 2$ varies depending on the tilt angle $\Phi 1$ of the interface 830*l*. In other words, as the tilt angle $\Phi 1$ of the interface 830*l* becomes greater, the extent to which the exit angle $\Phi 2$ varies may be larger.

The interface 830*l* may be a planar surface so that light incident on the optical scanner 830 may be refracted at the same angle and emitted at the same exit angle $\Phi 2$. The first and second fluids 831 and 832 may not be mixed together. For example, the first fluid 831 may be a polar liquid, and the second fluid 832 may be a gas or a non-polar liquid. Furthermore, the first and second fluids 831 and 832 may be light-transmissive fluids. The interface 830*l* between the first and second fluids 831 and 832 may undergo a change due to a voltage difference. To create a voltage difference, the optical scanner 830 may further include one or more pairs of electrodes that are separated from each other with the first and second fluids 831 and 832 interposed therebetween.

Referring to FIG. 9, an optical scanner 930 may further include first and second electrodes 933 and 934 separated from each other with the first and second fluids 931 and 932 interposed therebetween. The first and second electrodes 933 and 934 may be transparent, but are not limited thereto. Furthermore, hydrophobic insulating layers 935 and 936 may be formed on surfaces of the first and second electrodes 933 and 934, respectively, which are in contact with the first and second fluids 931 and 932. However, an exemplary embodiment is not limited thereto, and the first and second electrodes 933 and 934 may be hydrophobic electrodes. Thus, upon application of a voltage to the first and second electrodes 933 and 934, because of a surface tension, one of the first and second fluids 931 and 932 that is a polar fluid may flow so as to minimize an area thereof that is contact with the first and second electrodes 933 and 934 or with a non-polar fluid. For example, if the first fluid 931 is a polar fluid, the sum of a contact angle θ1 between the first fluid 931 and the first electrode 933 and a contact angle θ2 between the first fluid 931 and the second electrode 934 may be 180°. In other words, voltages may be applied to the first and second electrodes 933 and 934 so that the sum of the two contact angles θ1 and θ2 is 180°.

To scan internal organs having a tubular structure such as a small intestine and a large intestine, the above-described optical scanner and optical switch may be used. Use of the optical scanner and optical switch may allow irradiation of light to an object that is disposed at a side of an optical probe and emission of light over a wide range of regions without eliminating the need for rotating the optical probe itself.

Figure 10:
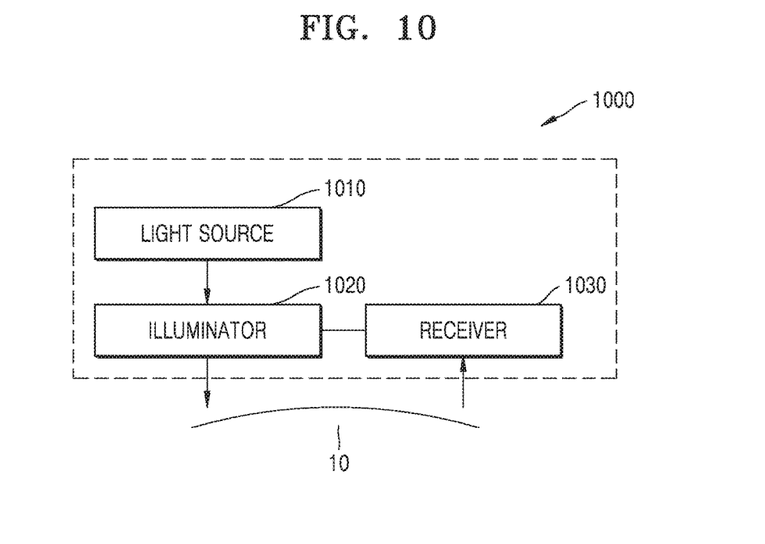
FIG. 10 is a block diagram of a medical imaging apparatus according to an exemplary embodiment.

The optical probes according to one or more of the above exemplary embodiments may be used as a component of a medical imaging apparatus. For example, the optical probe may be inserted into a body cavity to illuminate an object. FIG. 10 is a block diagram of a medical imaging apparatus 1000 according to an exemplary embodiment. The medical imaging apparatus 1000 according to the present exemplary embodiment may be an endoscope. Referring to FIG. 10, the medical imaging apparatus 1000 may include a light source 1010 for generating light, an illuminator 1020 for illuminating an object 10, and a receiver for receiving light reflected from the object 10. The above-described optical probe may be used as the illuminator 1020. The receiver 1030 may include at least one of a lens for enlarging light reflected from the object 10 and an imaging module for imaging reflected light. The illuminator 1020 and the receiver 1030 may be realized in separate probe bodies or may be combined into a single probe body. When the receiver 1030 includes an imaging module, the medical imaging apparatus 1000 may include at least one of a signal processor that performs signal processing on the result received from the imaging module to generate an image and a display for displaying an image.

Figure 11:
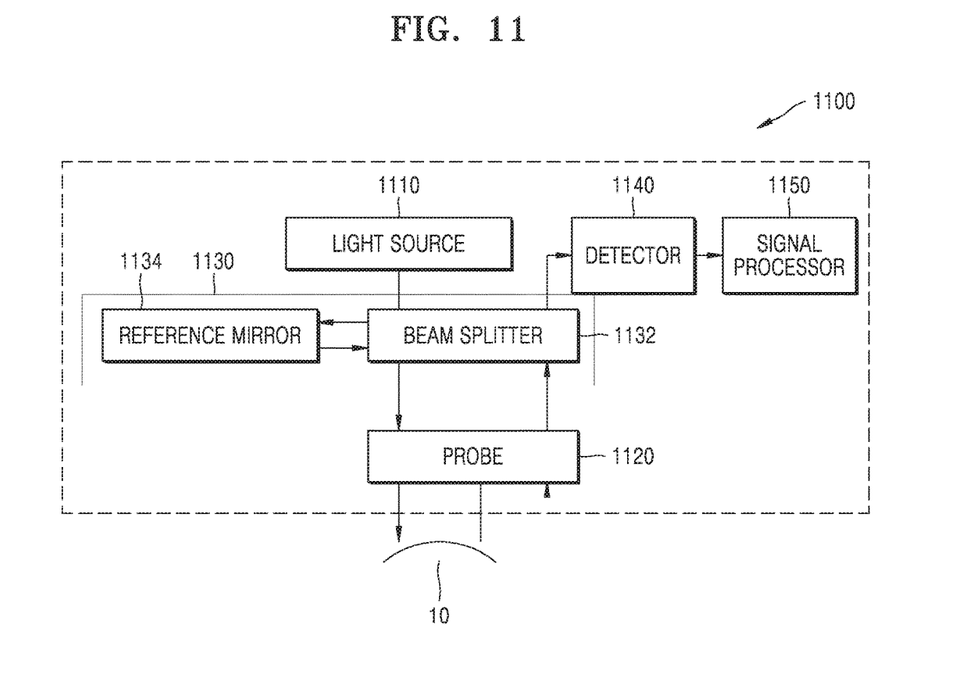
FIG. 11 is a block diagram of a medical imaging apparatus according to another exemplary embodiment.

FIG. 11 is a block diagram of a medical imaging apparatus 1100 according to another exemplary embodiment. Referring to FIG. 11, the medical imaging apparatus 1100 according to the present exemplary embodiment includes a light source 1110 that generates light, a probe 1120 that transmits light to an object 10 and receives light from the object 10, an optical interferometer that divides light emitted by the light source 1110 and directs part of the light onto the probe 1120 and causes interference between light received from the probe 1120 and reference light, a detector 1140 that detects an interference signal applied by the optical interferometer 1130, and a signal processor 1150 that processes a signal output from the detector 1140 to generate an image. The optical interferometer 1130 may include a beam splitter 1132 and a reference mirror 1134. The medical imaging apparatus 1100 may use an optical coherence tomography (OCT) technology.

The operation of the medical imaging apparatus 1100 will now be described. The light source 1110 generates light and delivers the light to the optical interferometer 1130. Light emitted by the light source 1110 is then split into a measurement beam and a reference beam. The measurement beam and the reference beam are sent to the probe 1120 and the reference mirror 1134, respectively, and are then reflected back into the beam splitter 1132.

The probe 1120 may transmit light as it scans a predetermined region of the object 10. For example, the probe 1120 may be one or a combination of the above-described optical probes. While a measurement beam delivered to the probe 1120 is irradiated by the probe 1120 onto the object 10 whose section images of an inner part will be acquired, a responding beam corresponding to the measurement beam reflected from the object 10 is sent to the beam splitter 1132 of the optical interferometer 1130 through the probe 1120. The beam splitter 1132 causes interference between the responding beam and a reference beam reflected from the reference mirror 1134, and the detector 1140 detects an interference signal. When the interference signal is delivered to the signal processor 1150, the signal processor 1150 acquires a cross-sectional image of the object 10. While it is described above for convenience of explanation that the probe 1120 may be one or more of the above-described optical probes, an exemplary embodiment is not limited thereto. For example, the probe 1120 may be divided into a first probe for transmitting light to the object 10 and a second probe for receiving light from the object 10.

Figure 12:
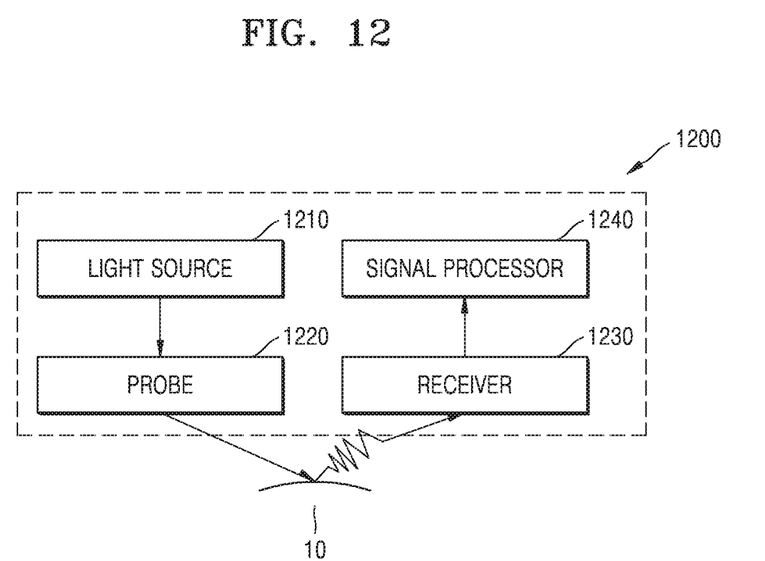
FIG. 12 is a block diagram of a structure of a medical imaging apparatus according to another exemplary embodiment.

FIG. 12 is a block diagram of a structure of a medical imaging apparatus 1200 according to another exemplary embodiment. Referring to FIG. 12, the medical imaging apparatus 1200 according to the present exemplary embodiment includes a light source 1210 that generates light, a probe 1220 that transmits light emitted by the light source 1210 to an object 10, a receiver 1230 that receives ultrasound waves from the object 10, and a signal processor 1150 that processes a signal received by the receiver 1230 to generate an image. The medical imaging apparatus 1200 may use a photoacoustic tomography (PAT) technology. The PAT technology is used to create an image by detecting a pressure wave that is generated in a tissue as the object 10 by irradiating a laser pulse. When a material such as a liquid or solid is irradiated with laser light, the material absorbs an optical energy to produce an instantaneous thermal energy and subsequently an acoustic wave due to a thermoelastic effect. Because a thermoelastic coefficient and an absorption rate for a wavelength of light vary depending on the type of a material of the object 10, ultrasound waves having different magnitudes may be generated for the same amount of light energy. By detecting these ultrasound waves, an image representing distributions of blood vessels and a microscopic change in structural features of a tissue inside a human body may be created using a non-invasive method.

The probe 1220 is configured to irradiate light by scanning a predetermined region of the object 10. For example, the probe 1220 may be one or a combination of the above-described optical probes.

When the probe 1220 irradiates light onto the object 10, an ultrasound wave is generated in the object 10. A frequency band or magnitude of the ultrasound wave may vary according to a pulse width and a pulse fluence of a laser and properties of the object 10 such absorption coefficient of a laser pulse, reflectance coefficient, specific heat, and thermal expansion coefficient. When the object 10 is irradiated with pulsed laser light, an ultrasound wave having a different magnitude or frequency band may be generated according to the type of the object 10, and may be detected to acquire an image that can distinguish or identify the type of the object 10.

The receiver 1230 may include a transducer for converting an ultrasound wave generated in the object 10 into an electrical signal. For example, the transducer may be a piezoelectric micromachined ultrasonic transducer (pMUT) for converting vibrations due to ultrasound waves into electrical signals. The pMUT may include materials showing a piezoelectric effect, such as a piezoelectric ceramic material, a single crystal material, and a composite piezoelectric material containing the piezoelectric ceramic or single crystal material and a polymer material. Alternatively, the transducer may be realized by a capacitive micromachined ultrasonic transducer (cMUT), a magnetic micromachined ultrasonic transducer (mMUT), or an optical ultrasonic detector. The signal processor 1240 may process a signal received from the receiver 1230 to generate an ultrasound image.

Although the above-described medical imaging apparatuses 100, 1100, and 1200 are constructed using endoscopy, OCT, and PAT technologies, the optical probes according to one or more of the above exemplary embodiments may be used in a wide variety of medical imaging apparatuses including a medical imaging apparatus using optical coherence microscopy (OCM). In this case, a receiver may include detection sensors suitable for kinds of signals generated in an object, and a suitable image signal processing method may be used.

An optical switch according to one or more of the above exemplary embodiments is configured to change a path of propagation of light according to a refractive index of a fluid introduced therein. Furthermore, an optical probe and a medical imaging apparatus according to exemplary embodiments including the optical switch allow scanning of objects disposed on the front of the optical probe as well as on sides of the object. Thus, the optical probe may be used to inspect various types of organs.

While one or more exemplary embodiments have been described with reference to the figures, it will be understood by one of ordinary skill in the art that various changes in form and details may be made therein without departing from the spirit and scope as defined by the following claims. Thus, it should be understood that the exemplary embodiments described therein should be considered in a descriptive sense only and not for purposes of limitation. The scope of the invention is defined not by the detailed description of the invention but by the appended claims, and all differences within the scope of the appended claims and their equivalents will be construed as being included in the present invention.

What is claimed is:

1. An optical probe comprising:
   a probe body that is configured to be insertable into a body cavity; and
   an optical switch that is disposed in the probe body and comprises:
      a first region formed of a material having a first refractive index;
      an interface of the first region, the interface being disposed between the first region and a second region; and
      the second region, formed by the interface and a transparent plate opposite the interface, is configured to have at least one opening to introduce one of a first fluid and a second fluid into the second region,
   wherein the interface is tapered such that a width of the interface decreases in a longitudinal direction of the probe body,
   wherein an inner surface of the transparent plate extends linearly in a perpendicular direction to the longitudinal direction of the probe body, the inner surface of the transparent plate facing the second region,
   wherein light propagates along the longitudinal direction of the probe body by successively passing through the transparent plate, the second region, the interface and the first region in response to the first fluid being introduced into the second region of the optical switch, the first fluid having the first refractive index, and
   wherein at least part of the light propagates in a lateral direction of the probe body by successively passing through the transparent plate and the second region and being reflected on the interface in response to the second fluid introduced into the second region, the second fluid having a second refractive index that is different from the first refractive index.

2. The optical probe of claim 1, wherein the interface is symmetric about a central axis of the probe body.

3. The optical probe of claim 1, further comprising:
   an optical fiber for delivering light to the optical switch, wherein the width of the interface decreases toward the optical fiber.

4. The optical probe of claim 3, wherein an angle between the interface and a central axis of the probe body is less than or equal to 90°-θi where θi is a critical angle for total reflection at the interface.

5. The optical probe of claim 1, wherein the at least one opening is connected to a fluid reservoir such that a plurality of different fluids may be selectively introduced into the second region.

6. The optical probe of claim 1, wherein the at least one opening is formed between the interface and the transparent plate.

7. The optical probe of claim 1, wherein the light is incident on a surface of the second region that is opposite the interface.

8. The optical probe of claim 7, wherein the light is incident perpendicularly on the surface of the second region that is opposite the interface.

9. The optical probe of claim 7, wherein the first fluid having the first refractive index and the second fluid having the second refractive index that is less than the first refractive index are selectively introduced into the second region.

10. The optical probe of claim 9, wherein the first fluid is a transparent liquid, and the second fluid is a transparent gas.

11. The optical probe of claim 9, wherein the second fluid is the same as fluid present in the probe body.

12. The optical probe of claim 1, wherein the first region is formed of a transparent solid material including at least one of plastic and glass.

13. The optical probe of claim 1, wherein the inner surface of the transparent plate extends parallel with an outer surface of the first region and perpendicular to the longitudinal direction of the probe body, the outer surface facing the optical probe and extending in the lateral direction of the probe body.

14. An optical switch comprising:
a first region formed of a material having a first refractive index;
an interface of the first region, the interface being disposed between the first region and a second region; and
the second region, formed by the interface and a transparent plate opposite the interface, having at least one opening to introduce one of a first fluid and a second fluid into the second region,
wherein the interface is tapered such that a width of the interface decreases in a longitudinal direction of the optical switch,
wherein an inner surface of the transparent plate extends linearly in a perpendicular direction to the longitudinal direction of the optical switch, the inner surface of the transparent plate facing the second region,
wherein light propagates along the longitudinal direction of the probe body by successively passing through the transparent plate, the second region, the interface and the first region in response to the first fluid being introduced into the second region of the optical switch, the first fluid having the first refractive index, and
wherein at least part of the light propagates in a lateral direction of the probe body by successively passing through the transparent plate and the second region and being reflected on the interface in response to the second fluid introduced into the second region, the second fluid having a second refractive index that is different from the first refractive index.

15. The optical switch of claim 14, wherein the interface is symmetric about a central axis across the first and second regions.

16. The optical switch of claim 14, wherein an angle between the interface and a central axis is less than or equal to 90°-θi where θi is a critical angle for total reflection at the interface.

17. The optical switch of claim 14, wherein the at least one opening is connected to a fluid reservoir such that a plurality of different fluids may be selectively introduced into the second region.

18. The optical switch of claim 14, wherein the first fluid having the first refractive index and the second fluid having the second refractive index less than the first refractive index are selectively introduced into the second region.

19. The optical switch of claim 18, wherein the first fluid is a transparent liquid, and the second fluid is a transparent gas.

20. A medical imaging apparatus comprising:
a light source for generating light;
an optical probe comprising:
a probe body that is configured to be insertable into a body cavity; and
an optical switch that is disposed in the probe body and comprises:
a first region formed of a material having a first refractive index;
an interface of the first region, the interface being disposed between the first region and a second region; and
the second region, formed by the interface and a transparent plate opposite the interface, is configured to have at least one opening to introduce one of a first fluid and a second fluid into the second region,
wherein the interface is tapered such that a width of the interface decreases in a longitudinal direction of the probe body,
wherein an inner surface of the transparent plate extends linearly in a perpendicular direction to the longitudinal direction of the probe body, the inner surface of the transparent plate facing the second region,
wherein the optical probe is configured to irradiate light generated by the light source onto an object,
wherein light propagates along the longitudinal direction of the probe body by successively passing through the transparent plate, the second region, the interface and the first region in response to the first fluid being introduced into the second region of the optical switch, the first fluid having the first refractive index, and
wherein at least part of the light propagates in a lateral direction of the probe body by successively passing through the transparent plate and the second region and being reflected on the interface in response to the second fluid introduced into the second region, the second fluid having a second refractive index that is different from the first refractive index.

* * * * *